(12) United States Patent
Schaz et al.

(10) Patent No.: US 11,871,938 B2
(45) Date of Patent: Jan. 16, 2024

(54) KEYLESS TOOL SHAFT COUPLING

(71) Applicant: Aesculap AG, Tuttlingen (DE)

(72) Inventors: Uwe Schaz, Neuhausen (DE); Roland-Alois Högerle, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 407 days.

(21) Appl. No.: 17/296,702

(22) PCT Filed: Nov. 29, 2019

(86) PCT No.: PCT/EP2019/083102
§ 371 (c)(1),
(2) Date: May 25, 2021

(87) PCT Pub. No.: WO2020/109557
PCT Pub. Date: Jun. 4, 2020

(65) Prior Publication Data
US 2022/0054146 A1    Feb. 24, 2022

(30) Foreign Application Priority Data
Nov. 30, 2018    (DE) .................... 10 2018 130 576.1

(51) Int. Cl.
*A61B 17/16*    (2006.01)
*A61B 17/14*    (2006.01)
*A61B 17/00*    (2006.01)

(52) U.S. Cl.
CPC ............ *A61B 17/162* (2013.01); *A61B 17/14* (2013.01); *A61B 2017/00477* (2013.01)

(58) Field of Classification Search
CPC .. A61B 2017/0046; A61B 2017/00464; A61B 2017/00469; A61B 2017/00473;
(Continued)

(56) References Cited

U.S. PATENT DOCUMENTS 4,829,857 A * 5/1989 Jones ................. B25G 3/18
                                                        81/177.1
5,871,493 A    2/1999 Sjostrom et al.
(Continued)

FOREIGN PATENT DOCUMENTS

DE    102014103345 A1    9/2015
EP        1790292 A1    5/2007
(Continued)

OTHER PUBLICATIONS

Written Opinion received in International Application No. PCT/EP2019/083102, dated Feb. 28, 2020, with translation, 12 pages.
(Continued)

*Primary Examiner* — Majid Jamialahmadi
(74) *Attorney, Agent, or Firm* — Christopher A. Rothe; Culhane Meadows PLLC

(57) ABSTRACT

A keyless coupling for a tool shaft and a handpiece of a surgical instrument having a first coupling section, which is provided on a proximal section of the tool shaft, a second coupling section, which is provided on a distal section of a shaft holder of the handpiece, and a locking/unlocking element. The locking/unlocking element is arranged on the tool shaft and forms a latching section, and the shaft holder has an undercut for receiving the latching section in a locking position of the two coupling sections such that the latching section and the undercut are in latching engagement with one another and secure the two coupling sections against a relative axial movement with respect to one another at least in the pulling direction.

9 Claims, 2 Drawing Sheets

(58) Field of Classification Search
CPC ...... A61B 2017/00862; A61B 2017/00477; A61B 17/14; A61B 17/162; B25G 3/18; B25G 3/12

See application file for complete search history.

(56) References Cited

U.S. PATENT DOCUMENTS

| | | |
|---|---|---|
| 10,603,094 B2 | 3/2020 | Wogoman et al. |
| 2011/0202043 A1 | 8/2011 | Eberle |
| 2013/0006253 A1 | 1/2013 | Waite et al. |
| 2013/0253482 A1 | 9/2013 | Dannoritzer |
| 2015/0012014 A1 | 1/2015 | Williams |
| 2015/0123357 A1 | 5/2015 | Stern |
| 2016/0074047 A1 | 3/2016 | Fritzinger et al. |

FOREIGN PATENT DOCUMENTS

| | | |
|---|---|---|
| EP | 2613726 B1 | 10/2016 |
| JP | 2007105485 A | 4/2007 |
| JP | 201313732 A | 1/2013 |
| JP | 2016193184 A | 11/2016 |
| WO | 2013167496 A1 | 11/2013 |

OTHER PUBLICATIONS

International Search Report received in Application No. PCT/EP2019/083102, dated Feb. 28, 2020, with translation, 5 pages.
Search Report received in German Application No. 10 2018 130 576.1 dated Oct. 24, 2019, with translation, 16 pages.
Office Action received in Japanese Application No. 2021-531245 dated Jun. 27, 2023, with translation, 5 pages.

* cited by examiner

KEYLESS TOOL SHAFT COUPLING

CROSS-REFERENCE TO RELATED APPLICATIONS

This application is the United States national phase entry of International Application No. PCT/EP2019/083102, filed Nov. 29, 2019, and claims the benefit of priority of German Application No. 10 2018 130 576.1, filed Nov. 30, 2018. The contents of International Application No. PCT/EP2019/083102 and German Application No. 10 2018 130 576.1 are incorporated by reference herein in their entireties.

FIELD

The invention relates to a keyless coupling for a tool shaft and a handpiece of a surgical instrument having a first coupling portion provided at a proximal portion of the tool shaft, a second coupling portion provided at a distal portion of a shaft receptacle of the handpiece, and a locking/unlocking element.

BACKGROUND

In the case of surgical instruments, in particular saws such as transversal saws, tool shafts, so-called tool shafts which have a slender diameter compared to the handpiece (drive handpiece) of the instrument, can be used with different lengths in order to provide the surgeon with good access to the surgical site, among other things by selecting the appropriate tool shaft length. Prior to surgical use, the selected tool shaft is mechanically coupled to the handpiece and is released from the handpiece again after completion of the surgical procedure in order to clean the tool shaft.

The mechanical connection and disconnection of the two coupling portions on the tool shaft and on the handpiece can be carried out either with the aid of a provided connecting tool or key or without tools in the form of a quick coupling.

Tool-shaft coupling/unlocking mechanisms are known from the prior art in which the coupling of the coupling portion on the tool shaft with the coupling portion on the handpiece is achieved by using a specially adapted or standardized coupling tool or key. For example, the tool shaft is coupled with the handpiece in a force-fit and/or form-fit manner by tightening a screw or clamping sleeve.

Connections using a designated tool, however, always have the disadvantage that the user has to expend a comparatively large amount of effort when coupling the instrument if he has to handle another additional part, namely the coupling tool. Furthermore, during the reprocessing cycle, there is a risk that the coupling tool may be lost during sterilization, for example, or may be assigned to the wrong sieve.

Alternative solutions in the prior art therefore provide for a tool-free or keyless connection of the two coupling portions, for example in the form of a form-fit connection by means of a locking/unlocking element on the handpiece, including in the form of a pushbutton or a rotatable sleeve.

However, couplings or locking/unlocking mechanisms using a locking/unlocking element arranged on the handpiece are technically complex, since the locking/unlocking element usually has to be decoupled from the moving/movable shaft receptacle. Moreover, a locking/unlocking element arranged on the handpiece poses the risk of unintentional unlocking during surgical use, since the surgeon usually holds and guides the handpiece in the locking/unlocking area during use. This creates a considerable risk for the patient.

SUMMARY

It is therefore the object of the invention to eliminate or at least reduce the disadvantages of the prior art. In particular, a tool-shaft coupling for a surgical instrument is to be created which enables the user to handle the locking/unlocking mechanism comfortably in a simple technical manner and minimizes any danger to the patient.

A basic idea of the invention is to provide a tool-shaft coupling operable without a tool/key for a surgical instrument with a locking/unlocking element which is arranged outside the (defined) holding area of the handpiece, more precisely which is arranged on the tool shaft itself.

Specifically, a keyless coupling or a keyless coupling mechanism or a locking/unlocking mechanism for a tool shaft and a handpiece of a surgical instrument, in particular a surgical (transversal) saw, is provided with a first coupling portion provided at a proximal (end) portion, preferably in a proximal half, of the tool shaft, a second coupling portion provided at a distal (end) portion of a shaft receptacle of the handpiece, and a locking/unlocking element. The locking/unlocking element is arranged on the tool shaft (as an integral part (thereof)) and forms a latch portion. The shaft receptacle has at least one undercut, in particular recess or (alternatively) cutout/strip-shaped projection, for example a passage opening or window, which is provided and adapted to receive the latch portion in a locking position of the two coupling portions in such a way that the latch portion and the undercut are in latching engagement with each other and secure the two coupling portions (and consequently the tool shaft and the shaft receptacle or the handpiece) against a relative axial movement to each other at least in the pulling direction, i.e. away from each other.

The term 'proximal' always refers to the end facing the user of the surgical instrument, while the term 'distal' always refers to the end facing away from the user.

Since the locking/unlocking element is located outside the (defined) holding area on the handpiece or basically outside the handpiece, unintentional release of the locking mechanism by the user during use of the surgical instrument is virtually impossible. The surgeon can therefore comfortably hold and guide the instrument on the handpiece without any risk to the patient from unintentional detachment of the tool shaft.

In particular, the latch portion can have a sliding surface that is inclined towards the proximal end of the tool shaft. When the tool shaft is inserted into the shaft receptacle, the locking/unlocking element can therefore independently enter the shaft receptacle (elastically yielding) by the latch portion sliding along its inclined sliding surface at the distal end of the shaft receptacle and finally snap into the undercut ('plug and play' coupling process).

In latching engagement, the latch portion and the undercut preferably also secure the two coupling portions against relative movement of the coupling portions in the circumferential direction. In this way, the two coupling portions are positioned such that they cannot rotate relative to each other, so that on the one hand the coupling is more stable, and on the other hand a torque can be transmitted from the shaft receptacle to the tool shaft.

Preferably, the preloading element is a flexible spring, in particular a needle spring, which is arranged at its one end to be rotatable about the same pivot axis as the locking/ unlocking element in the groove and in the radial direction of the tool shaft below the locking/unlocking element.

Preferably, the tool shaft has a guiding pocket on the inside which adjoins the groove in the proximal direction of the tool shaft and which is provided and adapted to receive the other end of the flexible spring and to limit a pivot radius of the flexible spring, in particular to prevent a pivoting movement of the flexible spring.

In an advantageous embodiment, the flexible spring and the locking/unlocking elements are mounted in the groove to be rotatable around a transverse pin, so that the flexible spring rests against the transverse pin and encloses its circumferential side almost completely, but at least more than 180°, and preferably 270°.

Preferably, the locking/unlocking element has an extension on its lower side in the radial direction of the tool shaft, so that the extension presses on the flexible spring from above in the coupled state, so that the spring is elastically deformed against its rest position in the locking position and pretensions the locking/unlocking element in a direction radially outward of the tool shaft.

Another advantage is that the groove bottom in the area of the transverse pin has a bulge with reduced wall thickness in order to provide sufficient installation space for the transverse pin and the flexible spring in contact with it and the locking/unlocking element, while the outer diameter of the tool shaft remains the same.

Further advantageously, the pivot radius of the locking/unlocking element in the unlocked state of the coupling portions is at least 45°, preferably at least 90°, particularly preferably 180°.

Preferably, the latch portion has a sliding surface sloping towards the proximal end of the tool shaft.

Preferably, the shaft receptacle has a plurality of, preferably two, three or four, undercuts/recesses spaced apart in the circumferential direction of the shaft receptacle, in particular evenly spaced apart, which are each provided and adapted to receive the latch portion in the locking position in such a way that they are in latching engagement with the latch portion. Advantageously, additional stabilization of the coupling can thus be achieved.

The locking/unlocking element has, in particular, an actuation portion which is provided and adapted to release the latch portion from the latching engagement with the undercut by manual actuation by the user and to release a relative axial displacement of the two coupling portions with respect to each other, at least in the direction of pull. Thus, advantageously, a particularly simple and convenient handling of the surgical device during decoupling is made possible, which is not subject to the risk of unintentional decoupling during using the device on the patient, since the actuation portion is not arranged on the handpiece or in the holding area of the handpiece, but on the tool shaft.

Preferably, at least the latch portion, in particular preferably the entire locking/unlocking element, is preloaded by means of a preloading element in a direction radially outward of the tool shaft. In this way, simple means can be used to ensure that the latch portion is held in the locking position in the undercut and that the latching engagement thus remains reliably in place until the preloading force is deliberately (manually) overcome.

In particular, the tool shaft has a groove extending essentially in its longitudinal direction, which is provided and adapted to accommodate the locking/unlocking element over its entire length. Part of the height of the locking/unlocking element is thus constructionally recessed into the tool shaft, enabling a compact design of the tool-shaft locking/unlocking element unit.

Preferably, the distal end of the locking/unlocking element is arranged/mounted in the groove to be rotatable about a pivot axis that runs transverse to the longitudinal axis of the tool shaft and the groove, so that the locking/unlocking element can be pivoted out of and into the groove. The pivoting movement enables the latch portion to be pivoted into and out of the undercut on the shaft receptacle, i.e. into its locking position.

Preferably, the preloading element is a flexible spring, for example a leaf spring or rod spring with a narrow width, in particular narrower than the groove width, or particularly preferably a wire or needle spring, which is arranged or mounted or fixed in the groove (along its longitudinal extension) at its one (distal) end so as to be rotatable about or on the same pivot axis as the locking/unlocking element, and is located below the locking/unlocking element in the radial direction of the tool shaft. This design advantageously enables a particularly compact construction of the tool shaft with the locking element.

Furthermore, the tool shaft can preferably have a guiding pocket inside/formed in the tool shaft, which adjoins the groove in the proximal direction of the tool shaft and which is provided and adapted to receive the other (proximal) end of the flexible spring and in particular to limit a pivot radius of the flexible spring or to completely prevent a pivoting movement of the flexible spring. On the one hand, this enables stable positioning of the flexible spring and, on the other hand, prevents the flexible spring from pivoting out of the groove of the tool shaft in the unlocked state of the coupling portion and posing a risk of injury to the user.

In particular, the pivot radius of the locking/unlocking element in the unlocked state of the coupling portions is at least 45°, preferably at least 90°, and particularly preferably 180°. In the unlocked state, the locking/unlocking element can thus pivot freely out of the groove within its specified pivot radius and release the groove together with the internal flexible spring and guiding pocket for a cleaning agent. The larger the specified pivot radius, the easier it is to access the groove, the guiding pocket and the flexible spring for cleaning.

BRIEF DESCRIPTION OF THE DRAWING FIGURES

The invention is described in more detail below by means of a preferred embodiment with reference to the accompanying drawing. The following is shown:

The figures are only schematic in nature and are intended solely for the purpose of understanding the invention. Identical elements are designated with the same reference signs.

DETAILED DESCRIPTION

Figures 1, 2:
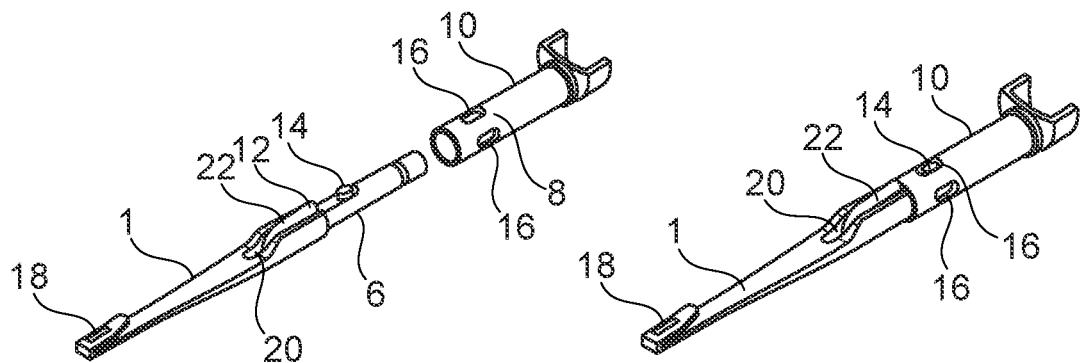
FIG. 1 shows a top perspective view of a tool shaft and a shaft receptacle in an uncoupled state according to one embodiment of the invention.
FIG. 2 shows a perspective top view of the tool shaft and the shaft receptacle in a coupled state according to the embodiment of the invention.

FIG. 1 shows in perspective plan view a coupling which can be operated without key for a (or of a) tool shaft 1 and a shaft receptacle 10, which is part of a handpiece 2 (shown in FIG. 3) for a (or of a) surgical instrument 4, with a first coupling portion 6 provided in a proximal portion of the tool shaft 1 and a second coupling portion 8 provided in a distal portion of the tool shaft 10, and a locking/unlocking element 12 arranged on the tool shaft 1 (not removable) and forming a latch portion 14. The (female) shaft receptacle 10 has at least one recess 16 (oriented perpendicular to the shaft receptacle direction) which is provided and adapted to receive the latch portion 14 in a locking position (shown in FIG. 2) of the two coupling portions 6, 8, so that the latch portion 14 and the recess 16 are in latching engagement with each other and secure the two coupling portions 6, 8 against relative axial movement with respect to each other at least in the pulling direction (shaft receptacle direction).

FIG. 1 shows the tool shaft 1 and the shaft receptacle 10 in an uncoupled state according to one embodiment of the invention. At the distal end of the tool shaft 1, an effector receptacle 18 is provided, for example for receiving a separate saw blade (not shown). Starting from the effector receptacle 18, the illustrated tool shaft 1 is flat up to approximately half of its longitudinal extension and increases in width and height/thickness (orthogonal to the longitudinal extension) towards the proximal end. This flat part of the tool shaft 1 is followed by a tool shaft portion of (essentially) round cross-section with a rounded transition, which has a circumferential annular groove in the region of its proximal end. The annular groove is used, for example, to hold the tool shaft in a cleaning holder for cleaning/disinfection/sterilization, for which purpose fixing elements, in particular resilient clamping plates, are provided on the cleaning holder, which engage in the annular groove and fix the shaft axially, preferably axially and radially. A chamfer is also provided at the proximal end of the tool shaft 1.

Starting from the rounded transition at the flat part to the tool shaft portion of round cross-section, an elongated groove 20 is made in the tool shaft 1 in the direction of the proximal end of the tool shaft 1, which extends along the longitudinal axis of the tool shaft 1 and whose width and length are matched to the width and length of the locking/unlocking element 12. The locking/unlocking element 12 is accommodated in the groove 20 up to part of its height. The locking/unlocking element 12 has a latch portion 14 in the form of a latch hook at its proximal end and an actuation portion 22 at its distal end, both of which project beyond the surface of the tool shaft 1 in the uncoupled state of the tool shaft 1. The longitudinal portion of the tool shaft 1, in which the latch portion 14 of the locking/unlocking element 12 is located up to the proximal end of the tool shaft 1, constitutes the first coupling portion 6 of the tool shaft 1.

The shaft receptacle 10, which is permanently installed in the handpiece 2 of a surgical instrument 4 (see FIG. 3), has a distal region in the form of a hollow cylinder, the inner diameter of which is matched to the outer diameter of the first coupling portion 6 in order to accommodate it. Following the hollow cylinder in the proximal direction is a widened, approximately crescent-shaped portion, to which the hollow cylinder is attached approximately centrally or is integrally formed. In the distal region of the hollow cylinder, four recesses 16 are provided in the form of passage openings or windows which are evenly spaced in the circumferential direction of the hollow cylinder. The size of the recesses 16 is selected such that the latch portion 14 can be accommodated therein. The longitudinal portion of the hollow cylinder, into which the first coupling portion 6 of the tool shaft 1 can be inserted until the latch portion 14 snaps into one of the recesses 16, forms the second coupling portion 8 of the shaft receptacle 10.

FIG. 2 is a perspective top view of the tool shaft 1 and the shaft receptacle 10 in the coupled state according to the embodiment of the invention. In the coupled state, the latch portion 14 is engaged in one of the recesses 16 and secures the coupling portions 6, 8 against axial pulling movement relative to each other. Relative rotational movement of the coupling portions 6, 8 is also prevented in the locked state of the latch portion 14 in the recess 16, since the longitudinally extending surfaces of the latch portion 14 come into contact with the longitudinally extending walls of the recess 16 and block rotational movement in a form-fit manner. Depending on the desired angular position of the effector receptacle 18 relative to the shaft receptacle 10 or to the handpiece 2, one of the four recesses 16 can be selected as the latch recess for the latch portion 14.

Figure 3:
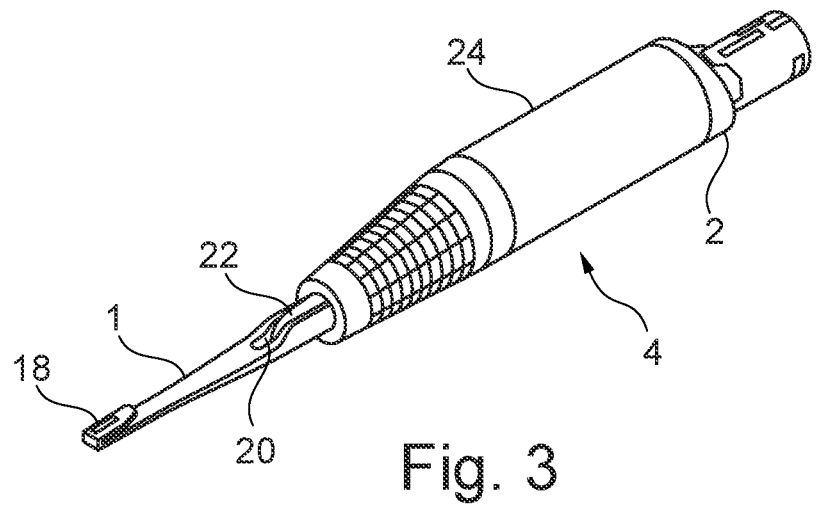
FIG. 3 shows a top perspective view of a surgical instrument with coupled tool shaft according to the embodiment of the invention.

FIG. 3 shows a perspective top view of a surgical instrument 4 with coupled tool shaft 1 according to the embodiment of the invention. The handpiece 2 of the surgical instrument 4 is shown with a handle region 24 for gripping and guiding the surgical instrument 4 by the user. The shaft receptacle 10 is installed inside the handpiece 2 and therefore not visible in FIG. 3. The coupled tool shaft 1 protrudes from the distal end of the handpiece 2 to such an extent that the actuation portion 22 of the locking/unlocking element 12 is located immediately distal to the handpiece 2, i.e. outside the handpiece 2.

Figure 4:
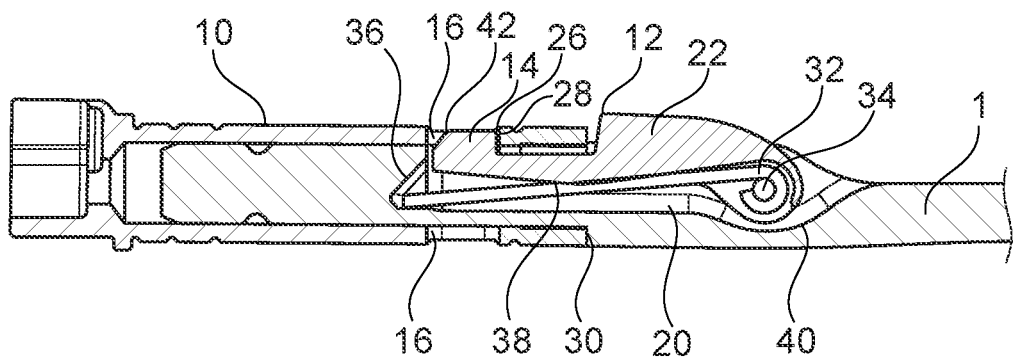
FIG. 4 shows a section of a longitudinal cut through the tool shaft and the shaft receptacle in a coupled state along line IV in FIG. 2.

FIG. 4 shows a section of a longitudinal view through the tool shaft 1 and the shaft receptacle 10 in the coupled state along line IV of FIG. 2. It can be seen that the latch portion 14 is engaged in a recess 16. Thereby, the latch portion 14 with a latching surface 26, which rises radially outward substantially perpendicular to the longitudinal extension of the tool shaft 1, comes into contact with a contact surface 28 of the recess 16, which is opposite the latching surface 26 in the coupled state, and thus blocks a pulling movement (relative axial movement away from each other) of the two coupling portions 6, 8 by form fit. It can also be seen that the tool shaft 1 forms a radial step or shoulder 30 on its side radially opposite the actuation element 22, the end face of which (side facing the shaft receptacle 10) comes into contact with a distal end face (side facing the tool shaft 1) of the shaft receptacle 10 and thus blocks a pushing movement (relative axial movement towards each other) of the two coupling portions 6, 8 by form fit. In the coupled state, the actuation element 22 itself assumes a height (extension in the radial direction of the tool shaft 1) that exceeds the surface/outer surface of the shaft receptacle 10, while the height of the latch portion 14 is selected such that it lies approximately flush with the surface of the shaft receptacle 10 in the coupled state. The longitudinal distance between the latch portion 14 and the actuation element 22 of the locking/unlocking element 12 minimally exceeds the longitudinal extent of the shaft receptacle 10 between its distal end and the recess 16, so that the portion of the shaft receptacle 10 between its distal end and the recess 16 is accommodated between the latch portion 14 and the actuation element 22 in the coupled state.

A flexible spring 32 is arranged below (radially inside) the locking/unlocking element 12. In this embodiment, the flexible spring 32 is a wire. Both the flexible spring 32 and the locking/unlocking element 12 are arranged or mounted rotatably about a transverse pin 34 in the groove 20. The transverse pin 34 thus forms a pivot axis for the locking/unlocking element 12 and the flexible spring 32 and is provided at the distal end or portion of the groove 20. The flexible spring 32 is in contact with the transverse pin 34 and surrounds its circumferential side almost completely, but at least more than 180°, and preferably 270°. Starting from the bend surrounding the transverse pin 34, the flexible spring 32 extends in the longitudinal direction of the groove 20 into a guiding pocket 36, which adjoins the groove 20 proximally and is inserted into the interior of the tool shaft 1, i.e. has no opening towards the circumferential side of the tool shaft 1. The guiding pocket 36 has a beveled wall surface in the radial direction towards the locking/unlocking element 12, which limits the pivot radius of the flexible spring 32 in the radial direction so that it cannot pivot out of the guiding pocket 36.

The distal end of the locking/unlocking element 12 rests against the bend of the flexible spring 32 surrounding the transverse pin 34 and surrounds the circumferential side of the flexible spring 32 preferably by more than 180°. On its lower side, the locking/unlocking element 12 shows an extension 38 in the radial direction of the tool shaft 1, which can be seen in FIG. 4 as a slight V-profile. In the coupled state, the extension 38 presses from above on the flexible spring 32 so that it is elastically deformed against its rest position and preloads the locking/unlocking element 12 in a direction radially outward of the tool shaft 1. In this way, the flexible spring 32 secures the latching engagement of the latch portion 14 in the recess 16. In the area of the transverse pin 34, the groove bottom has a bulge 40 with a reduced wall thickness in order to create sufficient installation space for the transverse pin 34 and the flexible spring 32 and locking/unlocking element 12 resting against it, while the outer diameter of the tool shaft 1 remains the same.

The transverse pin 34 itself is held in a through-hole (not shown) of the groove walls and is flush with the surface of the tool shaft 1. The transverse pin 34 is secured by an interference fit or by welding.

If the tool shaft 1 and the shaft receptacle 10 are to be coupled to each other, the two coupling portions 6, 8 are pushed into each other manually. The latch portion 14 slides along the distal end of the second coupling portion 8 on its inclined sliding surface 42 without manual actuation of the locking/unlocking element 12 and is pressed radially inward against the spring force of the flexible spring 32 until it has passed the longitudinal portion of the shaft receptacle 10 between its distal end and the recess 16 and snaps into the recess 16 due to the preloading force of the flexible spring 32.

If the tool shaft 1 and the shaft receptacle are to be decoupled from each other, the actuation portion 22 is manually pushed inward against the preloading force of the flexible spring 32, which also moves the latch portion 14 radially inward and out of the recess 16 so that the latching engagement of the latch portion 14 and the recess 16 is released and the tool shaft 1 can be manually pulled out of the shaft receptacle 10.

Figure 5:
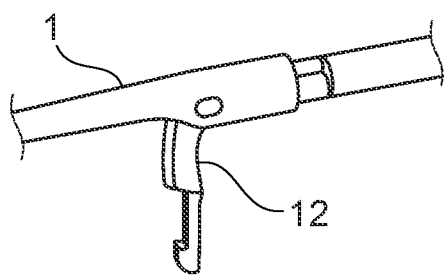
FIG. 5 shows a perspective side view of the tool shaft in a cleaning position.

FIG. 5 shows a perspective side view of the tool shaft 1 in a cleaning position. Once the tool shaft 1 is decoupled, it can be brought into its cleaning position by turning the locking/unlocking element 12 towards the lower side of the tool shaft 1. Due to gravity, the locking/unlocking element 12 pivots downward out of the groove 20, thereby exposing the groove 20 and giving access to flexible spring 32 and guiding pocket 36 for a cleaning agent and/or instrument. Since the guiding pocket 36 limits the pivot radius of the flexible spring 32, the flexible spring 32 does not leave the groove 20 but is held in the groove 20 and the guiding pocket 36 even in the cleaning position, which eliminates any risk of injury to the user by the flexible spring 36.

Figure 6:
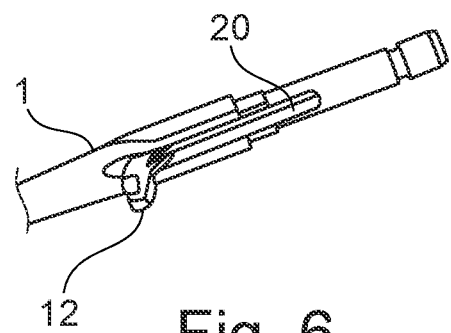
FIG. 6 shows a perspective bottom view of the tool shaft in the cleaning position.

FIG. 6 shows a perspective bottom view of the tool shaft 1 in the cleaning position. In this illustration, it can be seen how the groove 20 is exposed in the cleaning position.

Figure 7:
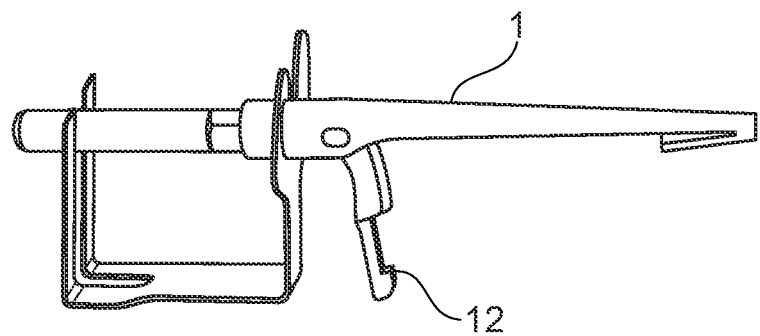
FIG. 7 shows a perspective side view of the tool shaft in a cleaning holder.

FIG. 7 shows a perspective side view of the tool shaft 1 in a cleaning holder. The cleaning holder supports the proximal portion of the tool shaft 1 essentially horizontally at a height at which the locking/unlocking element 12 can swing out of the groove as far as possible, preferably up to a vertical swing-out. The locking/unlocking element 12 can therefore be automatically swung out for mechanical cleaning.

In summary, the invention relates to a keyless coupling for a tool shaft 1 and a handpiece 2 of a surgical instrument 4, comprising a first coupling portion 6 provided at a proximal portion of the tool shaft 1, a second coupling portion 8 provided at a distal portion of a shaft receptacle 10 of the handpiece 2, and a locking/unlocking element 12, wherein the locking/unlocking element 12 is arranged on the tool shaft 1 and forms a latch portion 14 and the shaft receptacle 10 comprises at least one undercut, in particular a recess 16, which is provided and adapted to receive the latch portion 14 in a locking position of the two coupling portions 6, 8, so that the latch portion 14 and the undercut, in particular the recess 16, are in latching engagement with each other and secure the two coupling portions 6, 8 against relative axial movement with respect to each other at least in the pulling direction.

The invention claimed is:

1. A keyless coupling for a tool shaft and a handpiece of a surgical instrument, the keyless coupling comprising a first coupling portion provided at a proximal portion of the tool shaft, a second coupling portion provided at a distal portion of a shaft receptacle of the handpiece, and a locking/unlocking element, wherein:

the locking/unlocking element is arranged on the tool shaft and forms a latch portion and the shaft receptacle comprises at least one recess provided and adapted to receive the latch portion in a locking position of the first and second coupling portions so that the latch portion and the at least one recess are in latching engagement with each other and secure the first and second coupling portions against relative axial movement with respect to each other in a pulling direction and in a circumferential direction, wherein:

the locking/unlocking element is preloaded in the locking position by a preloading element in a direction radially outward of the tool shaft, wherein the preloading element is a flexible spring;

the tool shaft has a groove extending substantially in its longitudinal direction, wherein the groove is provided and adapted to receive the locking/unlocking element along its entire length;

the locking/unlocking element is arranged at its distal end to be rotatable about a pivot axis in the groove so that the locking/unlocking element is pivotable out of and into the groove; and wherein the preloading element and the locking/unlocking element are mounted rotatably about a transverse pin in the groove, and the preloading element bears against the transverse pin and partially surrounds a circumferential side of the transverse pin.

2. The keyless coupling according to claim 1, wherein the locking/unlocking element has an extension on its lower side in a radial direction of the tool shaft, so that the extension presses from above onto the preloading element in a coupled state, so that the preloading element is elastically deformed in the locking position against its rest position and pretensions the locking/unlocking element in a direction radially outward of the tool shaft.

3. The keyless coupling according to claim 1, wherein the groove comprises a bottom having a bulge in proximity to the transverse pin, the bulge having a reduced wall thickness in order to provide sufficient installation space for the transverse pin and the preloading element as well as the locking/unlocking element while an outer diameter of the tool shaft remains constant.

4. The keyless coupling according to claim 1, wherein the locking/unlocking element has a pivot radius in an unlocked state of the first and second coupling portions of at least 45°.

5. The keyless coupling according to claim 1, wherein the latch portion has a sliding surface sloping towards a proximal end of the tool shaft.

6. The keyless coupling according to claim 1, wherein the shaft receptacle has a plurality of undercuts spaced apart in the circumferential direction, the plurality of undercuts each provided and adapted to receive the latch portion in the locking position so as to be in latching engagement with the latch portion.

7. The keyless coupling according to claim 1, wherein the locking/unlocking element further comprises an actuation portion provided and adapted to release the latch portion from latching engagement with the recess by manual actuation and to release a relative axial displacement of the first and second coupling portions with respect to each other at least in the pulling direction.

8. The keyless coupling according to claim 1, wherein the preloading element comprises a first end and a second end, and is arranged to be rotatable at the first end about the pivot axis in the groove and in a radial direction of the tool shaft below the locking/unlocking element.

9. The keyless coupling according to claim 8, wherein the tool shaft has a guiding pocket that adjoins the groove in a proximal direction of the tool shaft and which is provided and adapted to receive the second end of the preloading element and to limit a pivot radius of the preloading element.

* * * * *